(12) United States Patent
Simmons et al.

(10) Patent No.: US 8,146,430 B2
(45) Date of Patent: Apr. 3, 2012

(54) METHOD AND APPARATUS FOR CONVEYING AN ULTRASONIC SENSOR ABOUT AN OUTER PERIPHERAL SURFACE OF A TUBE

(75) Inventors: Robert Allan Simmons, Beaumont (CA); John William Whytock, Spruce Grove (CA); Arthur Dubbledam, Ardrossan (CA); Jason Wiebe, Edmonton (CA); Paul Torstensen, Ardrossan (CA); Mark Dubbledam, Ardrossan (CA)

(73) Assignees: Jireh Industries Ltd., Alberta (CA); Metalogic Inspection Services Inc, Alberta (CA)

( * ) Notice: Subject to any disclaimer, the term of this patent is extended or adjusted under 35 U.S.C. 154(b) by 686 days.

(21) Appl. No.: 12/300,100

(22) PCT Filed: May 10, 2007

(86) PCT No.: PCT/CA2007/000852
§ 371 (c)(1),
(2), (4) Date: Nov. 7, 2008

(87) PCT Pub. No.: WO2007/128139
PCT Pub. Date: Nov. 15, 2007

(65) Prior Publication Data
US 2009/0114026 A1    May 7, 2009

Related U.S. Application Data

(60) Provisional application No. 60/799,012, filed on May 10, 2006.

(51) Int. Cl.
*G01N 29/265* (2006.01)

(52) U.S. Cl. ............................ 73/640; 73/592; 73/644
(58) Field of Classification Search .............. 73/86, 592, 73/640, 622, 638, 661, 866.5, 644
See application file for complete search history.

(56) References Cited

U.S. PATENT DOCUMENTS 2,908,161 A   10/1959   Bincer
3,602,036 A    8/1971   Peterson
(Continued)

FOREIGN PATENT DOCUMENTS

CA          1108743         9/1981
(Continued)

OTHER PUBLICATIONS

International Search Report and Written Opinion for PCT/CA2007/000852, filed May 10, 2007, published as WO 2007/128139, entitled "Method and Apparatus for Conveying an Ultrasonic Sensor about an Outer Peripheral Surface of a Tube" (7 pages).

*Primary Examiner* — J M Saint Surin
(74) *Attorney, Agent, or Firm* — Fish & Richardson P.C.

(57) ABSTRACT

A method & apparatus for conveying an ultrasonic sensor about an outer peripheral surface of a tube to perform a non-destructive evaluation thereof is disclosed. The ultrasonic sensor is mounted on a flexible tension link and the method involves extending the flexible tension link while urging an extended portion of the flexible tension link towards the outer peripheral surface of the tube at a plurality of locations along it's length, thereby causing the ultrasonic sensor to move through an arc in a direction circumferentially around the tube while maintaining ultrasonic coupling between the ultrasonic sensor and the tube.

30 Claims, 6 Drawing Sheets

U.S. PATENT DOCUMENTS

| | | | |
|---|---|---|---|
| 3,990,300 A | 11/1976 | Kossoff | |
| 4,216,403 A | 8/1980 | Krempl et al. | |
| 4,372,153 A | 2/1983 | Mann | |
| 4,530,242 A | 7/1985 | Sandhu | |
| 4,531,413 A | 7/1985 | Tsuchita et al. | |
| 4,655,085 A | 4/1987 | Tomizawa et al. | |
| 4,672,852 A | 6/1987 | Gugel et al. | |
| 5,313,837 A | 5/1994 | Haynes | |
| 5,571,968 A | 11/1996 | Buckley | |
| 5,581,037 A | 12/1996 | Kwun et al. | |
| 5,583,292 A | 12/1996 | Karbach et al. | |
| 5,619,423 A | 4/1997 | Scrantz | |
| 5,623,107 A | 4/1997 | Patterson, Sr. et al. | |
| 6,222,897 B1 | 4/2001 | Hatley et al. | |
| 6,246,235 B1 | 6/2001 | Lowden et al. | |
| 6,347,551 B1 | 2/2002 | Turpening et al. | |
| 6,497,159 B1 | 12/2002 | Lavoie | |
| 6,600,806 B1 | 7/2003 | Istar | |
| 6,834,993 B1 | 12/2004 | Staniforth | |
| 6,883,386 B2 * | 4/2005 | Osone et al. | 73/861.25 |
| 7,284,456 B2 * | 10/2007 | Lavoie | 73/866.5 |
| 7,950,298 B2 * | 5/2011 | Lavoie et al. | 73/866.5 |
| 2009/0235749 A1 * | 9/2009 | Ehara et al. | 73/622 |

FOREIGN PATENT DOCUMENTS

| | | |
|---|---|---|
| DE | 2936660 | 3/1981 |
| EP | 0 578 402 A1 | 1/1994 |
| EP | 0 633 451 A2 | 6/1994 |
| EP | 0 902 282 | 3/1999 |
| EP | 0 985 905 | 3/2000 |
| GB | 778168 | 7/1957 |
| GB | 2 012 047 A | 7/1979 |
| GB | 2 263 777 A | 8/1993 |
| JP | 58079153 | 5/1983 |
| JP | 59154353 | 9/1984 |
| JP | 60017352 | 1/1985 |
| JP | 60082962 | 5/1985 |
| JP | 63309840 | 12/1988 |
| WO | WO 92/06372 | 4/1992 |

* cited by examiner

METHOD AND APPARATUS FOR CONVEYING AN ULTRASONIC SENSOR ABOUT AN OUTER PERIPHERAL SURFACE OF A TUBE

CROSS-REFERENCE TO RELATED APPLICATIONS

This application is a national stage application of and claims the benefit of PCT/CA2007/000852 filed on May 10, 2007, now published as PCT publication No. WO 2007/128139, which claims the benefit of priority from U.S. Patent Application No. 60/799,012, filed May 10, 2006. Both applications are incorporated herein by reference as part of the specification of this application.

BACKGROUND OF THE INVENTION

1. Field of Invention

This invention relates generally to non-destructive evaluation of tubes and more particularly to non-destructive evaluation of a tube using an ultrasonic sensor.

2. Description of Related Art

Processing plants, such as power generation petrochemical and plants for example, make extensive use of metal tubing for delivering steam and other fluids to various process steps. Commonly, such tubes are constructed by welding together sections of tubing. In most applications, and specifically in safety critical applications, each and every weld must be inspected to confirm the integrity of the weld. Such inspections may be performed during the construction or commissioning of a plant, but there is also a need for ongoing periodic inspection of welds to look for signs of corrosion and/or cracking, for example.

In many plants pluralities of tubes are run in close proximity to each other, often so closely spaced apart that access to the tube for performing an inspection of the weld may be difficult. While it is convenient to use ultrasonic non-destructive evaluation techniques for examining defects in many types of metal structures, the accessibility has limited the use of ultrasonic examination for inspecting tubes.

Accordingly, other inspection techniques such as gamma radiography have typically been used to perform such inspections. Gamma radiography involves the use of radioactive isotopes, and during radiographic inspections, radiographic shielding barriers must generally be erected to protect personnel from harmful radiation. Accordingly, the work of welders and other construction workers may be interrupted when it becomes necessary to clear an area in proximity to a tube being inspected.

In general the use of radioactive inspection techniques may cause unacceptable health and safety risks, and regardless of storage, handling, and transportation practices that may be implemented, human error may still occur resulting in accidents.

Accordingly there is a need for improved methods of inspection of tubes.

SUMMARY OF THE INVENTION

In accordance with one aspect of the invention there is provided a method for conveying an ultrasonic sensor about an outer peripheral surface of a tube to perform a non-destructive evaluation thereof, the ultrasonic sensor being mounted on an extendible portion of a flexible tension link. The method involves extending the flexible tension link while urging the extended portion of the flexible tension link towards the outer peripheral surface of the tube at a plurality of locations along the extended portion to cause the ultrasonic sensor to move through an arc circumferentially around the tube while maintaining ultrasonic coupling between the ultrasonic sensor and the tube.

Extending may involve extending the flexible tension link to cause the ultrasonic sensor to be conveyed from a first location on the outer peripheral surface of the tube to a second location the outer peripheral surface of the tube, the second location being spaced apart from the first location by substantially one complete revolution around the circumference of the tube, and the method may further involve performing the non-destructive evaluation while retracting the flexible tension link to cause the ultrasonic sensor to move from the second location to the first location.

The method may involve causing a reference mark to be made on the tube at at least one of the first location and the second location.

The method may involve introducing an ultrasonic coupling fluid between the sensor and the outer peripheral surface of the tube to further facilitate ultrasonic coupling between the ultrasonic sensor and the tube.

Introducing the ultrasonic coupling fluid may involve delivering a flow of ultrasonic coupling fluid between the ultrasonic sensor and the outer peripheral surface of the tube.

The flexible tension link may include a plurality of linked elements and the ultrasonic sensor may be mounted on at least one of the linked elements, and maintaining ultrasonic coupling between the ultrasonic sensor and the tube may involve urging the at least one of the linked elements towards the outer peripheral surface of the tube such that the ultrasonic sensor is urged into contact with the outer peripheral surface of the tube.

The flexible tension link may include a plurality of linked elements and urging the extended portion of the flexible tension link may involve urging each of the plurality of linked elements toward the outer peripheral surface of the tube thereby causing the extended portion of the flexible tension link to wrap around the tube.

The flexible tension link may be housed in a frame and the ultrasonic sensor may be mounted on a distal end of the flexible tension link, and extending may involve causing the distal end to be extended from the frame.

A proximate end of the flexible tension link may be coupled to an actuator on the frame, and causing the distal end of the flexible tension link to be extended may involve actuating the actuator to cause the distal end of the flexible tension link to be extended from the frame.

The method may involve clamping the frame to the outer peripheral surface of the tube before extending the flexible tension link.

The outer periphery of the tube may include an accessible portion and an inaccessible portion, the inaccessible portion including a portion of the outer periphery of the tube having limited access due to a surrounding environment, and the clamping may involve clamping the frame to the accessible portion of the outer periphery of the tube.

The ultrasonic sensor may include a first ultrasonic sensor and the flexible tension link may include a first flexible tension link and the method may further include a second ultrasonic sensor mounted on a second flexible tension link, the first and second ultrasonic sensors being spaced apart, the method further involving extending the second flexible tension link while urging a second extended portion of the second flexible tension link towards the outer peripheral surface of the tube at a plurality of locations along the second extended portion to cause the second ultrasonic sensor to move through an arc circumferentially around the tube while maintaining ultrasonic coupling between the second ultrasonic sensor and the tube.

The method may involve locating a circumferential position of the ultrasonic sensor on the peripheral surface of the tube.

Locating the circumferential position may involve determining a displacement of the flexible tension link.

Determining the displacement may involve coupling an encoder to the flexible tension link, the encoder being operable to produce a position signal representing the displacement.

The ultrasonic sensor may be coupled to an analyzer, the analyzer being operable to transmit electrical stimuli to the ultrasonic sensor and to receive electrical signals from the ultrasonic sensor representing results of the non-destructive evaluation of the tube, and the method may further involve receiving the position signal at the analyzer and correlating the results with the circumferential position of the ultrasonic sensor.

In accordance with another aspect of the invention there is provided an apparatus for conveying an ultrasonic sensor about an outer peripheral surface of a tube to perform a non-destructive evaluation thereof. The apparatus includes a frame operably configured to engage the tube and a flexible tension link housed in the frame, the flexible tension link being operably configured to permit the ultrasonic sensor to be mounted thereto. The apparatus also includes an actuator coupled to the flexible tension link and operable to cause the flexible tension link to extend from the frame. The flexible tension link is operably configured to urge an extended portion of the flexible tension link towards the outer peripheral surface of the tube at a plurality of locations along the extended portion to cause the ultrasonic sensor to move through an arc circumferentially around the tube while maintaining ultrasonic coupling between the ultrasonic sensor and the tube.

The actuator is operably configured to extend the flexible tension link to cause the ultrasonic sensor to be conveyed from a first location on the outer peripheral surface of the tube to a second location the outer peripheral surface of the tube, the second location being spaced apart from the first location by substantially one complete revolution around the circumference of the tube, the actuator further being operably configured to retract the flexible tension link to cause the ultrasonic sensor to move from the second location to the first location while performing the non-destructive evaluation of the tube.

The apparatus may include a coupling fluid supply line operably configured to introduce an ultrasonic coupling fluid between the ultrasonic sensor and the outer peripheral surface of the tube to further facilitate ultrasonic coupling between the ultrasonic sensor and the tube.

The ultrasonic coupling fluid may include water.

The flexible tension link may include a plurality of linked elements and the ultrasonic sensor may be mounted on at least one of the linked elements, the at least one linked element further including a spring operable to urge the at least one of the linked element towards the outer peripheral surface of the tube such that the ultrasonic sensor is urged into contact with the outer peripheral surface of the tube.

The flexible tension link may include a plurality of linked elements and the apparatus may further include a plurality of springs operating between the linked elements to urge the extended portion of the flexible tension link toward the outer peripheral surface of the tube such that the extended portion wraps around the tube when the flexible tension link is extended.

The ultrasonic sensor may be mounted on a distal end of the flexible tension link and the actuator may be coupled to a proximate end of the flexible tension link and actuating the actuator may cause the proximate end to be displaced thereby causing the distal end is extended from the frame.

The actuator may include a rotateable drum located in the frame, the proximate end of the flexible tension link being coupled to the drum and an un-extended portion of the flexible tension link may wrap around the drum.

The frame may further include a clamp operable to clamp the frame to the outer peripheral surface of the tube.

The clamp may be operably configured to clamp the frame to an accessible portion of the outer periphery of the tube.

The ultrasonic sensor may include a first ultrasonic sensor and the flexible tension link may include a first flexible tension link and the apparatus may further include a second ultrasonic sensor mounted on a second flexible tension link, the first and second ultrasonic sensors being spaced apart, the apparatus further including a second flexible tension link housed in the frame, the second flexible tension link being operably configured to permit the second ultrasonic sensor to be mounted thereto, the flexible tension link being coupled to the actuator, the actuator being operable to cause the second flexible tension link to be extended from the frame. The second flexible tension link may be operably configured to urge a second extended portion of the second flexible tension link towards the outer peripheral surface of the tube at a plurality of locations along the second extended portion to cause the second ultrasonic sensor to move through an arc circumferentially around the tube while maintaining ultrasonic coupling between the second ultrasonic sensor and the tube.

The apparatus may include an encoder, coupled to one of the flexible tension link, the actuator, and the ultrasonic sensor, the encoder being operably configured to produce a position signal representing a circumferential position of the ultrasonic sensor on the peripheral surface of the tube.

The apparatus may include an analyzer coupled to the ultrasonic sensor, the analyzer being operable to transmit electrical stimuli to the ultrasonic sensor and to receive electrical signals from the ultrasonic sensor representing results of the non-destructive evaluation of the tube, the analyzer further comprising an input for receiving the position signal from the encoder, the analyzer being operably configured to correlate the results with the circumferential position of the ultrasonic sensor.

In accordance with another aspect of the invention there is provided an apparatus for conveying an ultrasonic sensor about an outer peripheral surface of a tube to perform a non-destructive evaluation thereof. The apparatus includes a frame operably configured to engage the tube and a flexible tension link housed in the frame, the flexible tension link being operably configured to permit the ultrasonic sensor to be mounted thereto. The apparatus also includes provisions for extending the flexible tension link from the frame and provisions for urging an extended portion of the flexible tension link towards the outer peripheral surface of the tube at a plurality of locations along the extended portion to cause the ultrasonic sensor to move through an arc circumferentially around the tube while maintaining ultrasonic coupling between the ultrasonic sensor and the tube.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention.

DETAILED DESCRIPTION

Figure 1:
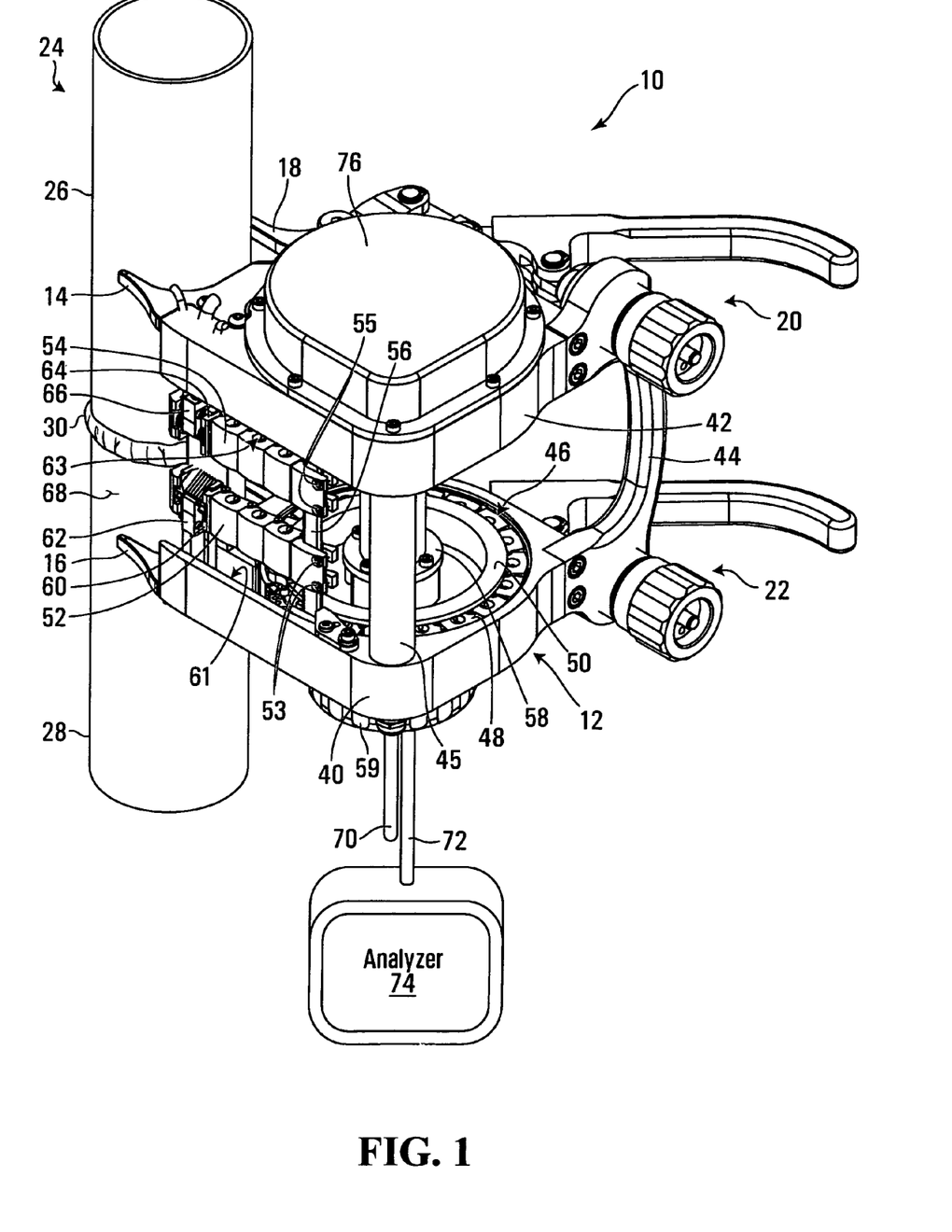
FIG. 1 is a perspective view of an apparatus in accordance with an embodiment of the invention for conveying an ultrasonic sensor about an outer peripheral surface of a tube.

Referring to FIG. 1, an apparatus for conveying an ultrasonic sensor about an outer peripheral surface of a tube 24 according to a first embodiment of the invention is shown generally at 10. In the embodiment shown, the tube 24 includes a first tube portion 26 and a second tube portion 28, the first and second tube portions being joined by a weld 30. The apparatus 10 is used to evaluate the quality of the weld 30, using ultrasonic non-destructive evaluation techniques.

The apparatus 10 includes a frame 12 and in this embodiment, the frame 12 includes a first frame portion 40 and a second frame portion 42. The first and second frame portions 40 and 42 are spaced apart by a plurality of cross members (only two cross members 44 and 45 shown in FIG. 1).

The frame 12 includes a pair of fixed clamp jaws 14 and 16 and a pair of spaced apart moveable clamp jaws 18, only one of which is shown in FIG. 1. Each of the moveable clamp jaws 18 has an associated clamp actuator 20 and 22 respectively. The clamp actuators 20 and 22 are operable to actuate the moveable jaws 18 to clamp the frame 12 to the tube 24 on which it is desired to perform a non destructive evaluation.

Figure 2:
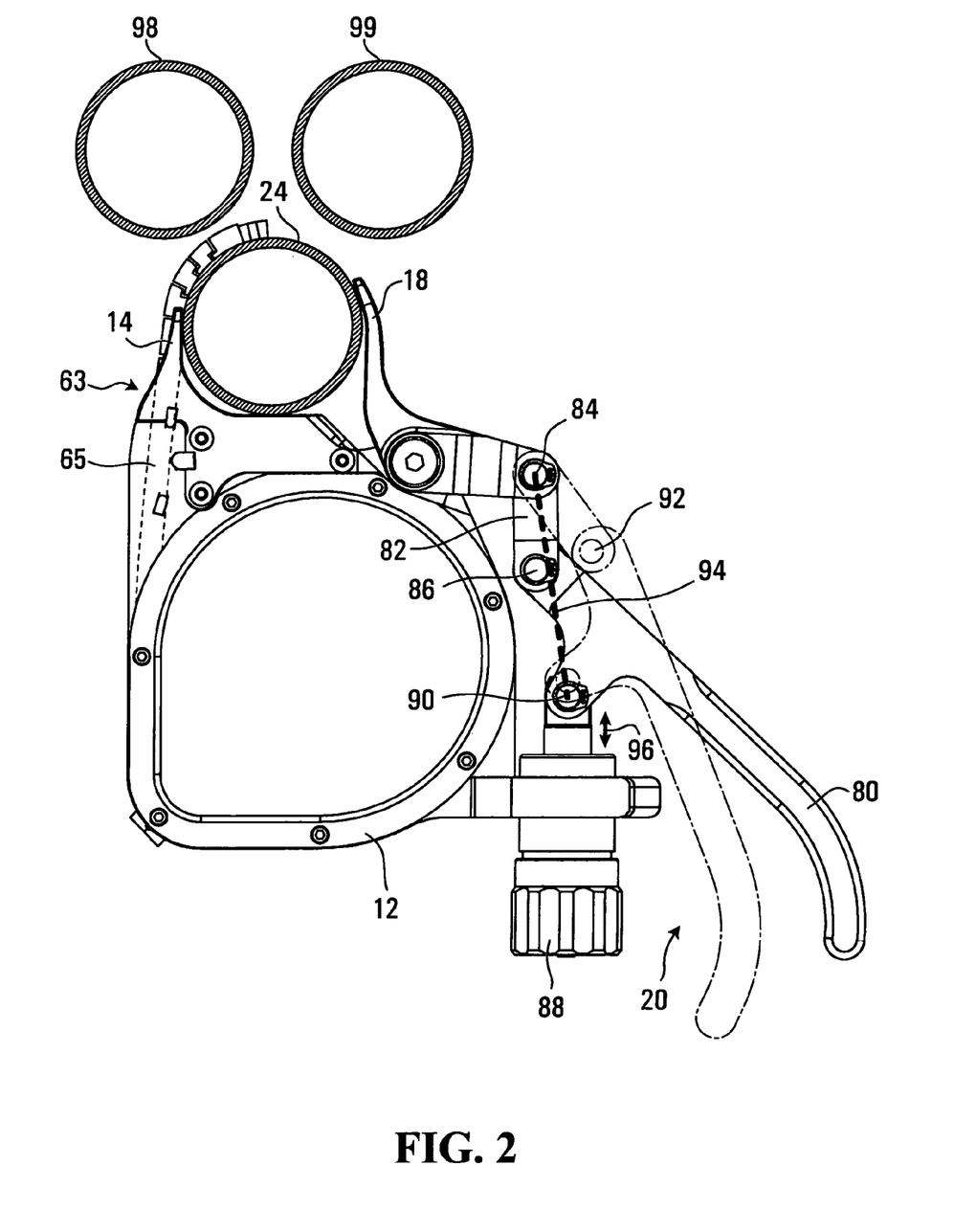
FIG. 2 is a top view of the apparatus shown in FIG. 1.

The clamp actuator 20 is shown in greater detail in FIG. 2, and includes a lever 80 which is coupled to the moveable jaw 18 by a linkage 82 fastened between the lever and the moveable jaw at first and second pivot pins 84 and 86. The clamp actuator also includes an adjustment screw 88 which is coupled to the lever 80 at a third pivot pin 90 to move the third pivot pin toward and away from the first pivot pin 84.

The clamp actuator 20 operates as an over-center clamp, and when the lever 80 is shifted toward the frame 12, the second pivot pin 86 is moved away from the frame 12 to a position 92 (shown in broken outline) causing the moveable jaw 18 to be urged toward the fixed jaw 14, thus clamping to the tube 24. Since the second pivot pin 86 is shifted past a center line 94 (drawn between the first pivot pin 84 and the third pivot pin 90) the lever 80 becomes locked in the location shown in broken outline. The adjustment screw 88 is operable to shift the location of third pivot pin 90 in the direction indicated by the arrow 96, facilitating clamping to tubes of varying diameter, and also facilitating adjustment of a clamping force for a particular tube diameter. Applying a force to the lever 80 in a direction away from the frame 12, causes the second pivot pin 86 to move past the center line 94 toward the frame, thus unlocking the moveable clamp jaw 18.

The apparatus 10 further includes a first flexible tension link 46 and a first drum 50. The first drum 50 is located in the first frame portion 40. In the embodiment shown in FIG. 1, the flexible tension link 46 includes a first portion 48, which is wrapped around and coupled to the first drum 50. The flexible tension link 46 also includes a second portion 52, which is spaced inwardly from the first frame portion 40.

Figure 3:
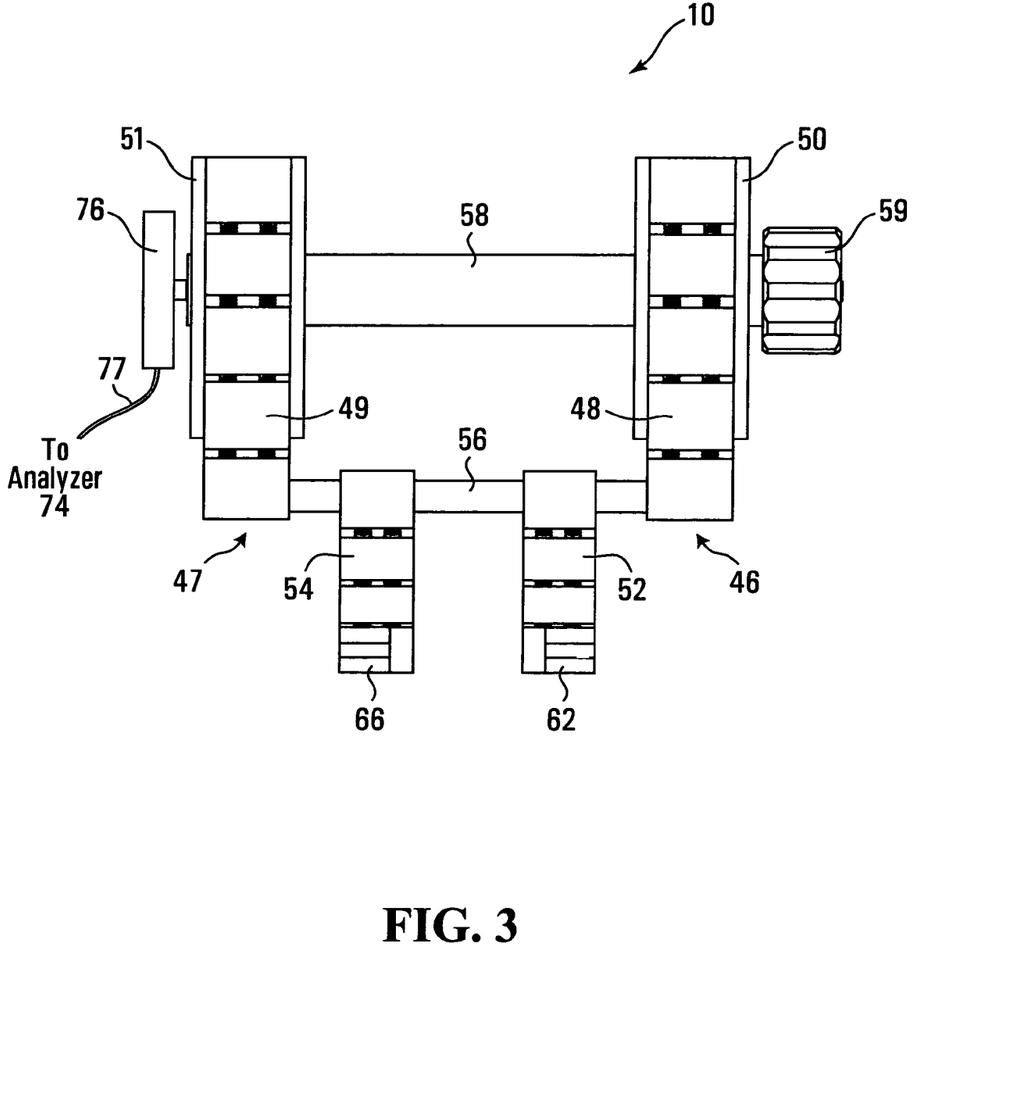
FIG. 3 is a side view of the apparatus shown in FIG. 1 with a frame portion removed.

The apparatus 10 is shown in FIG. 3 with the frame 12 removed to more clearly show elements which are obscured by the second frame portion 42 in FIG. 1. Referring to FIG. 3, the apparatus 10 further includes a second flexible tension link 47 and a second drum 51. The second drum 51 is located in the second frame portion 42 (shown in FIG. 1). The second flexible tension link 47 includes a first portion 49, which is wrapped around and coupled to the second drum 51.

Referring back to FIG. 1, the second tension link 47 also includes a second portion 54, which is spaced inwardly from the second frame portion 42.

The apparatus 10 further includes a bar 56, which is coupled to the first portions 48 and 49 of the first and second flexible tension links 46 and 47. The second portions 52 and 54 of the first and second flexible tension links 46 and 47 are slideably mounted on the bar 56 and each include a pair of fasteners 53 and 55 for securing the second portions at desired positions on the bar 56. Each of the second portions 52 and 54 may be positioned on the bar 56 by loosening the fasteners 53 and 55, sliding the second portions to respective desired positions on the bar 56, and then tightening the fasteners, thus securing the second portions to the bar in a desired spacing.

The spaced apart second portions 52 and 54 of the first and second flexible tension links permit the second portions to be extended through substantially a complete revolution around the circumference of the tube 24, without being impeded by the first portions 48 and 49 of the first and second flexible tension links 46 and 47.

As best shown in FIG. 3, the apparatus 10 also includes an actuator shaft 58 and an actuator knob 59. The actuator knob 59 is coupled to the actuator shaft 58. The actuator shaft 58 is located between, and coupled to, the first drum 50 and the second drum 51. When the actuator knob 59 is rotated thus rotating the first and second drums 50 and 51, the first and second portions 48 and 49 of the first and second flexible tension links 46 and 47 are extended (or retracted) thus extending (or retracting) the bar 56 and the second portions 52 and 54 of the first and second flexible tension links respectively.

Referring back to FIG. 1, the first frame portion 40 further includes a first guide 61 and the second frame portion 42 includes a second guide 63. Referring now to FIG. 2, the first guide 61 includes a channel 65 (shown in hidden detail in FIG. 2), which guides the flexible tension link 46 between the drum 50 and the tube 24. Similarly the second guide 63 includes a channel (not shown), which guides the flexible tension link 47 between the drum 51 and the tube 24.

Figure 4:
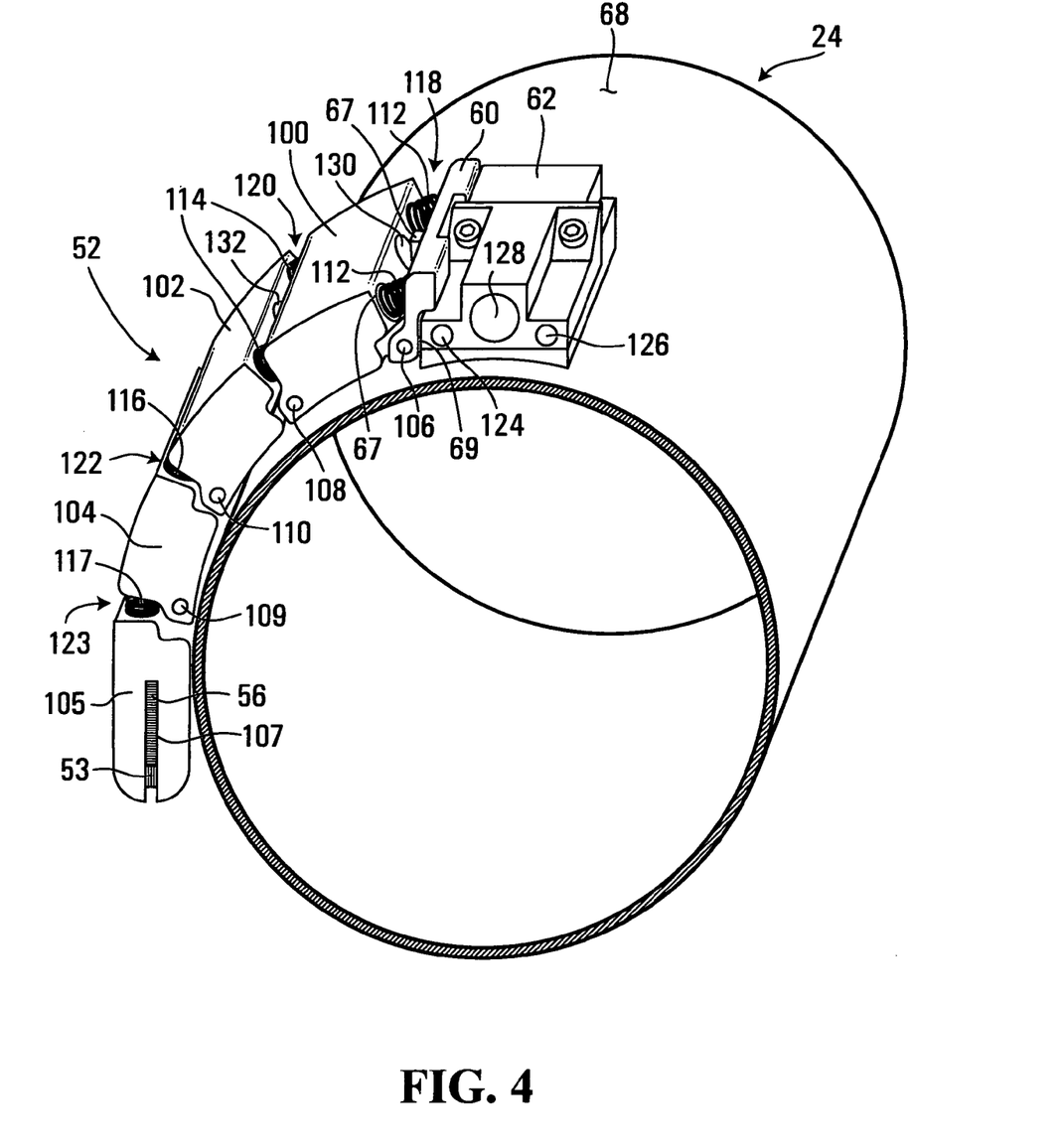
FIG. 4 is a perspective view of a portion of flexible tension link used in the apparatus shown in FIG. 1.

Referring now to FIG. 4, the second portion 52 of the first flexible tension link 46 includes a distal linked element 60. The distal linked element 60 includes a mounting face 69 for mounting an ultrasonic sensor 62. The ultrasonic sensor 62 includes a threaded hole (not shown) and is secured to the mounting face 69 by a threaded fastener 67 through the distal linked element 60.

Referring back to FIG. 1, the second portion 54 of the second flexible tension link 47 also includes a distal linked element 64 (similar to the element 60 shown in FIG. 4) for mounting an ultrasonic sensor 66.

In accordance with one aspect of the invention, the flexible tension links 46 and 47 are operably configured to urge an extended portion of each of the flexible tension links towards an outer peripheral surface 68 of the tube 24 at a plurality of locations along the extended portion to cause the ultrasonic sensor 62 and 66 to move through an arc circumferentially around the tube while maintaining ultrasonic coupling between the ultrasonic sensor and the tube.

Referring to FIG. 4, the second portion 52 of the flexible tension link 46 is shown in greater detail. The second portion 52 includes the distal linked element 60, and four linked elements 100, 102, 104, and 105. In general the flexible tension link 46 may include many linked elements similar to the linked elements 100-104. The distal linked element 60 is pivotally connected to the linked element 100 using a pin 106. Similarly the linked elements 100 and 102 are pivotally connected using a pin 108, and the linked elements 102 and 104 are pivotally connected using a pin 110.

In the embodiment shown in FIG. 4, the linked element 104 is connected to a linked element 105 using a pin 109. The linked element 105 includes a slot 107, which is shaped to receive the bar 56 for facilitating sliding connection of the linked element 105 to the bar 56 (as shown in FIG. 1 and as described above).

The second portion 54 of the second flexible tension link 47 is identical to the second portion 52 of the flexible tension link 46.

The second portion 52 of the flexible tension link 46 also includes first, second third, and fourth helical spring pairs 112, 114, 116 and 117 at first, second, third and fourth locations 118, 120, 122, and 123 respectively, along the length of the flexible tension link. In general, further spring pairs may be located between other linked elements along the flexible tension link 47. The first spring pair 112 is operable to urge the distal linked element 60 and the linked element 100 apart, the second spring pair 114 is operable to urge the linked element 100 and the linked element 102 apart, the third spring pair 116 is operable to urge the linked element 102 and the linked element 104 apart, and the fourth spring pair 117 is operable to urge the linked element 104 and the linked element 105 apart, thus causing the flexible tension link 46 to take on an arc shape that generally wraps around and conforms to the peripheral surface 68 of the tube 24 being evaluated, thus causing the ultrasonic sensor 62 to move through an arc circumferentially around the tube. The first spring pair 112 is further operable to urge the ultrasonic sensor 62 into contact with the peripheral surface 68 of the tube 24, thus facilitating ultrasonic coupling between the sensor and the tube.

Still referring to FIG. 4, in one embodiment the ultrasonic sensor 62 includes first and second coupling fluid ports 124 and 126 for introducing an ultrasonic coupling fluid between the sensor and the outer peripheral surface 68 of the tube to further facilitate ultrasonic coupling between the ultrasonic sensor and the tube. In this embodiment the ultrasonic coupling fluid comprises water, and the water is allowed to flow between the sensor and the outer peripheral surface 68 while performing the non destructive evaluation of the tube 24.

The ultrasonic sensor 62 also includes an electrical signal connector 128 for connecting a signal cable (not shown) for transmitting electrical stimuli to the ultrasonic sensor for receiving electrical signals from the ultrasonic sensor representing results of the non-destructive evaluation of the tube.

In this embodiment the linked elements 100 and 102 further include conduits 130 and 132 through which the coupling fluid supply line and the signal line may be threaded. Other linked elements may also include a conduit, thus allowing the coupling fluid supply line and the signal line to be run along the length of the flexible tension links 46 and 47 to couple to the sensors 62 and 66.

Referring back to FIG. 1, the apparatus 10 further includes a main coupling fluid supply line 70. The main coupling fluid supply line 70 includes a "Y" or "T" coupling (not shown) which splits the main fluid supply line into two separate supply lines for supplying coupling fluid to each of the sensors 62 and 66 respectively through the first and second coupling fluid ports.

The apparatus 10 also includes a main signal line 72, which includes a plurality of signal conductors including first signal conductors for coupling to the sensor 62, second signal conductors for coupling to the sensor 66, and third signal conductors for coupling to a rotary encoder 76, which is described later herein.

The main signal line 72 is coupled to an analyzer 74. The analyzer 74 includes circuitry which is operable to transmit electrical stimuli to the ultrasonic sensors 62 and 66 and circuitry which is operable to receive electrical signals from the ultrasonic sensor representing results of the non-destructive evaluation of the tube. The analyzer further includes circuitry and/or microprocessor circuits for analyzing the return signals and displaying an inspection result. Such analyzers for interfacing to one or more phased array ultrasonic sensors are commonly available, and in one embodiment the analyzer used may be a 32-channel ultrasound phased-array instrument (model number X-32) available from Harfang Microtechniques of Quebec Canada.

Referring to FIG. 3, the apparatus 10 further includes a rotary encoder 76, having a position signal output 77. The rotary encoder is coupled to the actuator shaft 58 and produces a position signal at the output 77 representing a displacement of the first and second flexible tension links when the actuator knob 59 is rotated. In this embodiment the encoder used is model number S6S supplied by US Digital of Vancouver, Wash. The 6S6 encoder is a high resolution rotary to digital converter which produces TTL-compatible signal outputs representing an angular position and/or velocity of the actuator shaft 58, and hence the position of first drum 50 and the second drum 51, which are coupled to the actuator shaft.

The position signal output 77 is coupled to the analyzer 74 via the third signal conductors in the main signal line 72 for transmitting the position signal to the analyzer. The analyzer 74 is operably configured to receive the position signal and to calculate the displacement of the first and second flexible tension links using the diameter of the first and second drums to convert angular position received from the encoder into a corresponding linear displacement of the flexible tension links.

Figure 5:
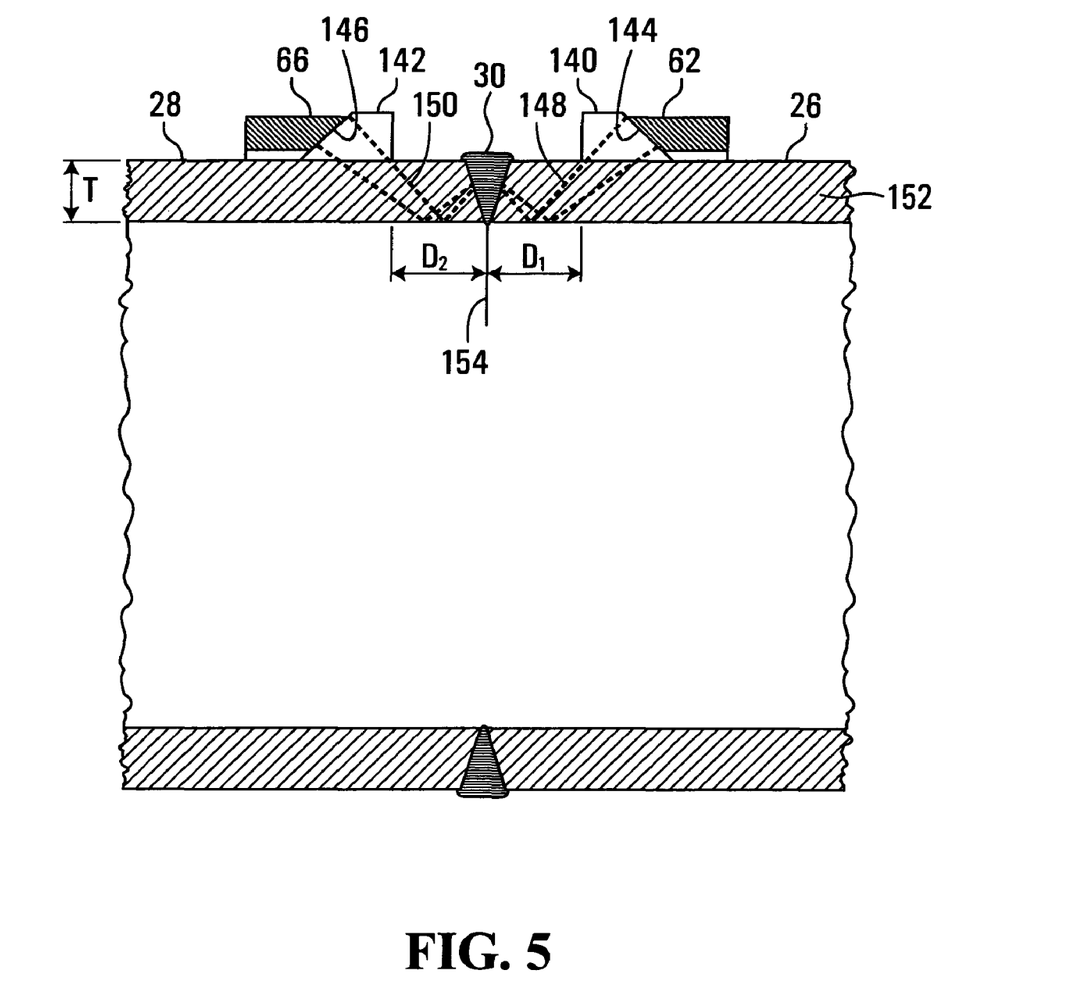
FIG. 5 is a cross sectional view of a welded tube.

The sensors 62 and 66 are shown in greater detail in FIG. 5. Referring to FIG. 5, each of the sensors 62 and 66 is mounted on wedges 140 and 142 respectively. Each of the wedges 140 and 142 includes an angled face 144 and 146 respectively. In one embodiment sensors 62 and 66 include a plurality of sensor elements (not shown) arranged in an array proximate the angled faces 144 and 146. Such multiple-element sensors are suitable for operation as a phased array, where the timing of excitation pulses sent to each of the sensor elements by the analyzer 74, may be controlled to focus and direct resulting ultrasonic beams 148 and 150 within a wall 152 of the tube 24, thus facilitating scanning of the sides of the weld 30 for defects.

Operation

The operation of the apparatus 10 shown in FIG. 1 is described with reference to FIG. 6 and FIGS. 1-5. The operation of the apparatus 10 is described in connection with the inspection of a weld joining two tubular sections although it should be understood that the apparatus may be used to evaluate defects in tubes other than weld related defects.

Figure 6:
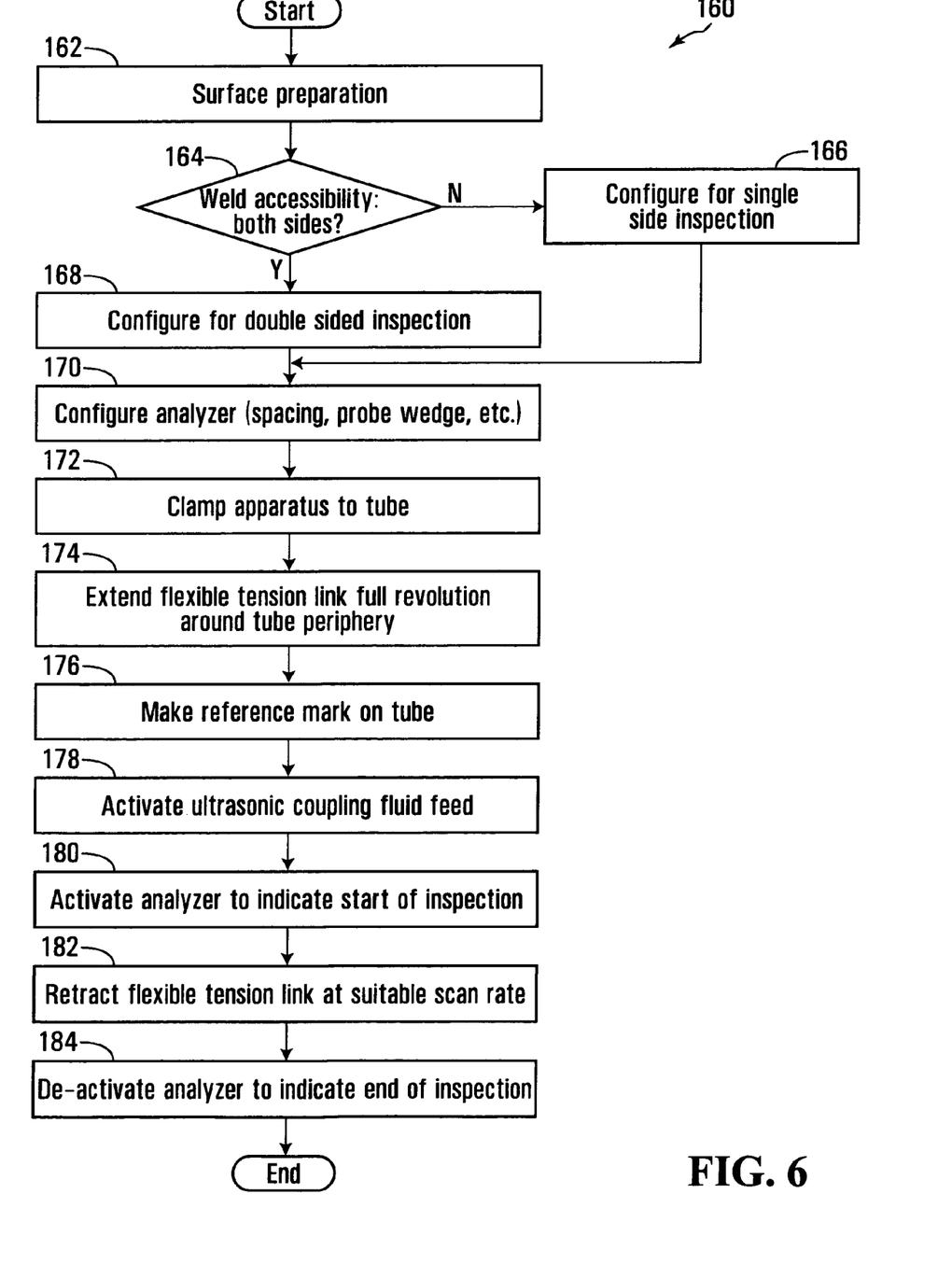
FIG. 6 is a process flowchart schematically depicting a process for performing a non-destructive evaluation of a tube, in accordance with an embodiment of the invention.

Referring to FIG. 6, a process for performing an ultrasonic non-destructive evaluation of a tube weld is shown generally at 160. As shown at 162, the process begins with preparing the surface of the tube to be inspected, which involves ensuring that the peripheral surface 68 over which the sensors 62 and 66 will be conveyed is free of weld spatter, dirt, grease, loose scale etc.

As shown at 164, where the weld 30 is only accessible from one side due to the surrounding environment, the apparatus 10 may be configured for single sided inspection at 166 by configuring the analyzer 74 to ignore the result from one of the sensors, and/or by removing the inactive sensor from the apparatus 10. The remaining description of the operation assumes that the apparatus 10 is configured for double sided inspection as shown at 168.

As shown at 170, the process continues with configuring the analyzer 74 and the apparatus 10 for correct sensor spacing, the type of sensor being used, etc. For example, referring to FIG. 5, the spacing "D1" and "D2" between the wedges 140 and 142 and a centerline 154 of the weld 30 should be within certain ranges, depending on a thickness "T" of the wall 152. Accordingly, if the spacing of the wedges 140 and 142 is not within the acceptable range, then the spacing of the second portions 52 and 54 of the first and second flexible tension links 47 and 47 may require adjustment as described above. It may be necessary to enter other information regarding the sensor configuration, such as angle of the angled faces 144 and 146, into the analyzer prior to performing the inspection.

Returning to FIG. 6 as shown at 172 the apparatus is then clamped to the tube 24 as described above, taking care to ensure that the spacing "D1" and "D2" (shown in FIG. 5) remain in the appropriate ranges (i.e. the apparatus is clamped in alignment with the centerline 154 of the weld 30). Alternatively, the configuration shown at 170 may be performed after clamping the apparatus 10 to the tube 24, should the access be sufficient to permit configuration of sensor spacing after clamping.

As shown at 174, the process continues by extending the flexible tension links 46 and 47 by rotating the actuator knob 59. The flexible tension links 46 and 47 are extended by one full revolution around the circumference of the tube 24 to a starting position for the inspection of the tube 24.

Referring to FIG. 4, as the flexible tension links are extended, the extended portion (e.g. the second portion 52) is urged towards the outer peripheral surface 68 of the tube 24 at a plurality of locations (e.g. the locations 118, 120 and 122) along the extended portion. This causes the sensor 62 to be urged into contact with the tube 24 while the second portion 52 wraps around the tube thus moving through an arc circumferentially around the tube. Advantageously, this allows the apparatus 10 to be used to perform inspections on a range of different tube diameters.

Referring back to FIG. 6, as shown at 176, a reference mark is then made to indicate the position of the sensors 62 and 66 at the starting position for the inspection. The reference mark may be useful if a defect is found in the tube 24, since the location of the defect indicated by the analyzer 74 is generally referenced to the start position. Accordingly should it be necessary to correct the defect or to cut the tube 24 for further inspection, the position of the defect, as indicated by the analyzer, may be located on the tube by measuring from the reference mark.

As shown at 178, at this stage in the process, the ultrasonic coupling fluid supply is activated to supply coupling fluid between the sensors 62 and 66 and the peripheral surface 68 of the tube 24.

As shown at 180, the inspection then commences by activating the analyzer 74. Generally activating the inspection involves pressing a "Start", "Record" or other button on the analyzer 74 to cause the analyzer to generate excitation signals and receive return signals from the sensors 62 and 66 and the encoder 76.

As shown at 182, the actuator knob 59 is then rotated to cause the flexible tension links 46 and 47 to be retracted into the frame 12, thus causing the sensors 62 and 66 to move through an arc in a direction circumferentially around the tube while maintaining ultrasonic coupling between the ultrasonic sensors and the tube 24. Once inspection has commenced the analyzer 74 monitors the position signal received from the encoder 76, from which the analyzer is able to determine a real time velocity of the sensors along the peripheral surface 68, and to provide feedback to the operator. The feedback may take the form of a plurality of indicator lights that show, for example, an indication such as "too fast", "too slow", or "correct" retraction speed. If the sensors 62 and 66 are conveyed too fast over the peripheral surface 68, defects may be missed.

As the flexible tension links 46 and 47 are retracted into the frame 12, the analyzer provides excitation signals to the sensors 62 and 66, which cause the ultrasonic beams 148 and 150 to be scanned over the weld 30 (as shown in FIG. 5). The sensors 62 and 66 also generate return signals, which are received by the analyzer 74, correlated with the position signal, and presented to the operator as data or a graphical interpretation thereof showing the result of the inspection.

While retracting the flexible tension links 46 and 47, the extended portions of the flexible tension links are urged towards the outer peripheral surface of the tube at a plurality of locations along the extended portion, as described above in connection with the extension, shown at 174.

Once the flexible tension links 46 and 47 have been fully retracted into the frame 12, the analyzer 74 is de-activated to indicate the end of the inspection, as shown at 184. The apparatus may then be unclamped and removed from the tube 24.

It has been discovered that it is advantageous to perform the inspection while retracting the flexible tension links 46 and 47, since the retraction movement is smoother than the extension movement. While it is possible to perform the inspection when extending the flexible tension links 46 and 47, it was found that the sensors 62 and 66 are more likely to stick while being extended, resulting in a less smooth movement and thus affecting the inspection result.

Advantageously, the relatively low profile of the sensors 62 and 66, shown in FIG. 5, and the mounting of the sensors on distal ends of the flexible tension links 46 and 47, permits inspection of a tube 24, even where the tube is surrounded by other tubes (such as tubes 98 and 99 shown in FIG. 2). In one embodiment the sensors 62 and 66 and the flexible tension links 46 and 47 have a profile height of less than 0.5 inches, allowing inspection of tubes that are spaced apart from the tube 24 by as little as 0.5 inches.

Alternative Embodiments

While the apparatus 10 has been described with reference to a hand operated actuator knob 59 for extending and retracting the flexible tension links 46 and 47, the actuator shaft 58 may also be coupled to a motor or other mechanism for automatically extending and retracting the flexible tension links.

While the apparatus 10 has been described as being configured using two phased array sensors 62 and 66, the apparatus may also be configured with a single sensor (or more than two sensors), and the sensor need not be a phased array ultrasonic sensor. Furthermore while the apparatus 10 includes a flexible tension link 46 and 47 having first and second spaced apart portions the sensor may also be mounted on a flexible tension link having only a single, in-line portion. However, such a configuration may not permit a full scan of the circumference of the tube 24, without unclamping, shifting circumferentially, and then re-clamping the apparatus.

While specific embodiments of the invention have been described and illustrated, such embodiments should be considered illustrative of the invention only and not as limiting the invention as construed in accordance with the accompanying claims.

What is claimed is:

1. A method for conveying an ultrasonic sensor about an outer peripheral surface of a tube to perform a non-destructive evaluation thereof, the ultrasonic sensor being mounted on an extendible portion of a flexible tension link, the method comprising:
   extending the flexible tension link while urging the extended portion of the flexible tension link towards the outer peripheral surface of the tube at a plurality of locations along the extended portion to cause the ultrasonic sensor to move through an arc circumferentially around the tube while maintaining ultrasonic coupling between the ultrasonic sensor and the tube.

2. The method of claim 1 wherein said extending comprises extending the flexible tension link to cause the ultrasonic sensor to be conveyed from a first location on the outer peripheral surface of the tube to a second location on the outer peripheral surface of the tube, said second location being spaced apart from said first location by substantially one complete revolution around the circumference of the tube, and further comprising performing the non-destructive evaluation while retracting the flexible tension link to cause the ultrasonic sensor to move from said second location to said first location.

3. The method of claim 2 further comprising causing a reference mark to be made on the tube at least one of said first location and said second location.

4. The method of claim 1 further comprising introducing an ultrasonic coupling fluid between the sensor and the outer peripheral surface of the tube to further facilitate ultrasonic coupling between the ultrasonic sensor and the tube.

5. The method of claim 2 wherein introducing said ultrasonic coupling fluid comprises delivering a flow of ultrasonic coupling fluid between the ultrasonic sensor and the outer peripheral surface of the tube.

6. The method of claim 1 wherein the flexible tension link comprises a plurality of linked elements and the ultrasonic sensor is mounted on at least one of said linked elements, and wherein maintaining ultrasonic coupling between the ultrasonic sensor and the tube comprises urging said at least one of said linked elements towards the outer peripheral surface of the tube such that the ultrasonic sensor is urged into contact with the outer peripheral surface of the tube.

7. The method of claim 1 wherein the flexible tension link comprises a plurality of linked elements and wherein urging said extended portion of the flexible tension link comprises urging each of said plurality of linked elements toward the outer peripheral surface of the tube thereby causing said extended portion of the flexible tension link to wrap around the tube.

8. The method of claim 1 wherein the flexible tension link is housed in a frame and the ultrasonic sensor is mounted on a distal end of the flexible tension link and wherein extending comprises causing said distal end to be extended from said frame.

9. The method of claim 8 wherein a proximate end of the flexible tension link is coupled to an actuator on the frame, and wherein causing said distal end of the flexible tension link to be extended comprises actuating said actuator to cause said distal end of the flexible tension link to be extended from said frame.

10. The method of claim 8 further comprising clamping said frame to the outer peripheral surface of the tube before extending the flexible tension link.

11. The method of claim 10 wherein the outer periphery of the tube comprises an accessible portion and an inaccessible portion, said inaccessible portion comprising a portion of the outer periphery of said tube having limited access due to a surrounding environment, and wherein said clamping comprises clamping said frame to said accessible portion of the outer periphery of the tube.

12. The method of claim 1 wherein the ultrasonic sensor comprises a first ultrasonic sensor and the flexible tension link comprises a first flexible tension link and further comprising a second ultrasonic sensor mounted on a second flexible tension link, said first and second ultrasonic sensors being spaced apart, the method further comprising:
   extending the second flexible tension link while urging a second extended portion of the second flexible tension link towards the outer peripheral surface of the tube at a plurality of locations along the second extended portion to cause the second ultrasonic sensor to move through an arc circumferentially around the tube while maintaining ultrasonic coupling between the second ultrasonic sensor and the tube.

13. The method of claim 1 further comprising locating a circumferential position of the ultrasonic sensor on the peripheral surface of the tube.

14. The method of claim 13 wherein locating said circumferential position comprises determining a displacement of the flexible tension link.

15. The method of claim 14 wherein determining said displacement comprises coupling an encoder to the flexible tension link, said encoder being operable to produce a position signal representing said displacement.

16. The method of claim 15 wherein the ultrasonic sensor is coupled to an analyzer, said analyzer being operable to transmit electrical stimuli to the ultrasonic sensor and to receive electrical signals from the ultrasonic sensor representing results of the non-destructive evaluation of the tube, and further comprising receiving said position signal at the analyzer and correlating said results with said circumferential position of the ultrasonic sensor.

17. An apparatus for conveying an ultrasonic sensor about an outer peripheral surface of a tube to perform a non-destructive evaluation thereof, the apparatus comprising:
   a frame operably configured to engage the tube;
   a flexible tension link housed in said frame, said flexible tension link being operably configured to permit the ultrasonic sensor to be mounted thereto;
   an actuator coupled to said flexible tension link and operable to cause said flexible tension link to be extended from said frame; and said flexible tension link being operably configured to urge an extended portion of the flexible tension link towards the outer peripheral surface of the tube at a plurality of locations along the extended portion to cause the ultrasonic sensor to move through an arc circumferentially around the tube while maintaining ultrasonic coupling between the ultrasonic sensor and the tube.

18. The apparatus of claim 17 wherein said actuator is operably configured to extend the flexible tension link to cause the ultrasonic sensor to be conveyed from a first location on the outer peripheral surface of the tube to a second location on the outer peripheral surface of the tube, said second location being spaced apart from said first location by substantially one complete revolution around the circumference of the tube, said actuator further being operably configured to retract the flexible tension link to cause the ultrasonic sensor to move from said second location to said first location while performing the non-destructive evaluation of the tube.

19. The apparatus of claim 17 further comprising a coupling fluid supply line operably configured to introduce an ultrasonic coupling fluid between the ultrasonic sensor and the outer peripheral surface of the tube to further facilitate ultrasonic coupling between the ultrasonic sensor and the tube.

20. The apparatus of claim 19 wherein said ultrasonic coupling fluid comprises water.

21. The apparatus of claim 17 wherein said flexible tension link comprises a plurality of linked elements and the ultrasonic sensor is mounted on at least one of said linked elements, said at least one of said linked element further comprising a spring operable to urge said at least one linked element towards the outer peripheral surface of the tube such that the ultrasonic sensor is urged into contact with the outer peripheral surface of the tube.

22. The apparatus of claim 17 wherein said flexible tension link comprises a plurality of linked elements and further comprising a plurality of springs operating between said linked elements to urge said extended portion of the flexible tension link toward the outer peripheral surface of the tube such that said extended portion wraps around the tube when the flexible tension link is extended.

23. The apparatus of claim 17 wherein the ultrasonic sensor is mounted on a distal end of said flexible tension link and wherein said actuator is coupled to a proximate end of said flexible tension link and whereby actuating said actuator causes said proximate end to be displaced thereby causing said distal end is extended from said frame.

24. The apparatus of claim 23 wherein said actuator comprises a rotateable drum located in said frame, said proximate end of said flexible tension link being coupled to said drum and wherein an un-extended portion of said flexible tension link wraps around said drum.

25. The apparatus of claim 23 wherein said frame further comprises a clamp operable to clamp the frame to the outer peripheral surface of the tube.

26. The apparatus of claim 25 wherein said clamp is operably configured to clamp said frame to an accessible portion of the outer periphery of the tube.

27. The apparatus of claim 17 wherein the ultrasonic sensor comprises a first ultrasonic sensor and said flexible tension link comprises a first flexible tension link and further comprising a second ultrasonic sensor mounted on a second flexible tension link, said first and second ultrasonic sensors being spaced apart, the apparatus further comprising:
a second flexible tension link housed in said frame, said second flexible tension link being operably configured to permit the second ultrasonic sensor to be mounted thereto;
said flexible tension link being coupled to said actuator, said actuator being operable to cause said second flexible tension link to be extended from said frame; and
said second flexible tension link being operably configured to urge a second extended portion of the second flexible tension link towards the outer peripheral surface of the tube at a plurality of locations along the second extended portion to cause the second ultrasonic sensor to move through an arc circumferentially around the tube while maintaining ultrasonic coupling between the second ultrasonic sensor and the tube.

28. The apparatus of claim 17 further comprising an encoder, coupled to one of said flexible tension link, said actuator, and the ultrasonic sensor, said encoder being operably configured to produce a position signal representing a circumferential position of the ultrasonic sensor on the peripheral surface of the tube.

29. The apparatus of claim 28 further comprising an analyzer coupled to the ultrasonic sensor, said analyzer being operable to transmit electrical stimuli to the ultrasonic sensor and to receive electrical signals from the ultrasonic sensor representing results of the non-destructive evaluation of the tube, said analyzer further comprising an input for receiving said position signal from said encoder, said analyzer being operably configured to correlate said results with said circumferential position of the ultrasonic sensor.

30. An apparatus for conveying an ultrasonic sensor about an outer peripheral surface of a tube to perform a non-destructive evaluation thereof, the apparatus comprising:
a frame operably configured to engage the tube;
a flexible tension link housed in said frame, said flexible tension link being operably configured to permit the ultrasonic sensor to be mounted thereto;
means for extending the flexible tension link from said frame; and
means for urging an extended portion of the flexible tension link towards the outer peripheral surface of the tube at a plurality of locations along the extended portion to cause the ultrasonic sensor to move through an arc circumferentially around the tube while maintaining ultrasonic coupling between the ultrasonic sensor and the tube.

* * * * *